United States Patent [19]

Vargas Garcia

[11] Patent Number: 4,616,634
[45] Date of Patent: Oct. 14, 1986

[54] SOFT TISSUE PROTECTOR FOR USE IN ORAL AND MAXILLOFACIAL SURGERY

[75] Inventor: Arturo Vargas Garcia, Rio Piedras, P.R.

[73] Assignee: Commonwealth of Puerto Rico, P.R.

[21] Appl. No.: 709,226

[22] Filed: Mar. 7, 1985

[51] Int. Cl.⁴ ............................................. A61B 17/02
[52] U.S. Cl. .................................................... 128/20
[58] Field of Search ...................... 128/20, 303 R, 305, 128/304

[56] References Cited

U.S. PATENT DOCUMENTS 4,147,167 4/1979 Hickmann ............................. 128/20

Primary Examiner—Jay N. Eskovitz
Attorney, Agent, or Firm—Scrivener Clarke Scrivener & Johnson

[57] ABSTRACT

A unitary instrument for protection and retraction of the soft tissues of the oral cavity during oral and maxillofacial surgery has a central handle part and active blade parts extending from the ends of the handle parts at different curvatures, with oppositely and differently curved blade extremities for adaptation to the relatively inaccessible areas of the maxillofacial region.

1 Claim, 4 Drawing Figures

SOFT TISSUE PROTECTOR FOR USE IN ORAL AND MAXILLOFACIAL SURGERY

On instrument for use in retracting and protecting soft tissue of the oral cavity during oral and maxillofacial surgery has an elongated linear handle part at the ends of which are diverging operative blades which extend from the handle at different angles which, respectively, adapt themselves to the mandibular, mentories and pterygomaxillary anatomic areas.

Figure 1:
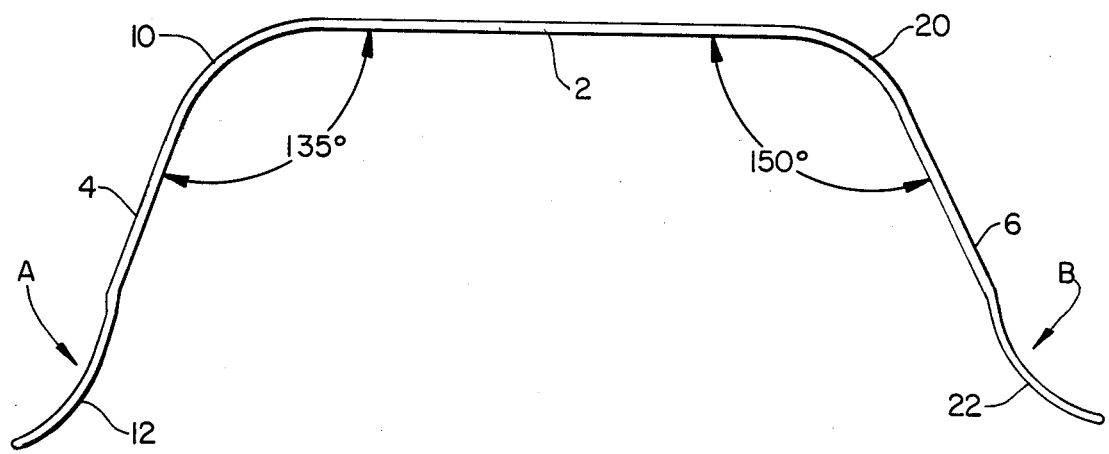
FIG. 1 is a side view of the instrument.

The invention provides an instrument for protecting and retracting the soft tissues in the relatively inaccessible areas of the maxillofacial region, thus facilitating the performance of specific surgical procedures in which protection and retraction of tissues are simultaneously required, such as mandibular fractures and correction of dento-facial deformities.

The preferred form of the invention is disclosed in the drawings and comprises a central handle part 2 which is linear in configuration, a first active blade part 4, and a second active blade part 6. The instrument is preferally made of 1/16 inch stainless steel with high corrosion resistance, which is necessary for surgical equipment, and the angles of its parts adapt themselves to the mandibular, mental and pterygomaxillary anatomic area.

The first active blade 4 forms a unitary extension of the handle part and extends from that part at an angle of approximately 135°, being connected to the handle part by an arcuate section 10. The outer end part of the blade is formed into a flat curved part 12 which extends from the outer end of the blade for a distance of approximately 40% of the length of the blade, which is preferably approximately two inches in length, and this curved part is reduced in thickness by removal of the material of the blade and is slightly enlarged in width.

Figure 2:
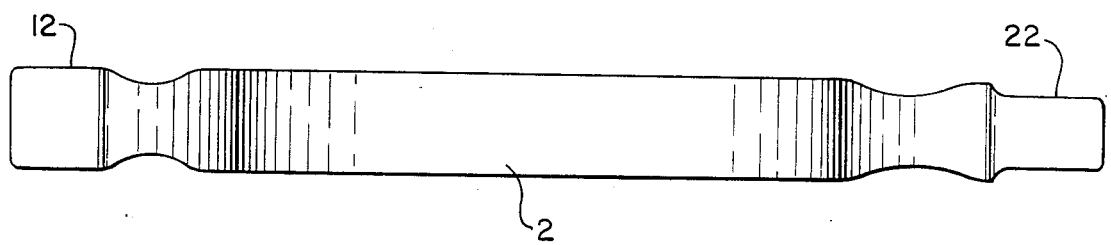
FIG. 2 is a bottom plan view.
Figure 3:
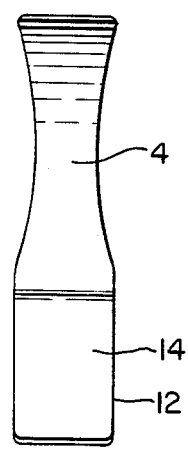
FIG. 3 is a view of the left end of the instrument, taken in the direction of arrow A of FIG. 1.
Figure 4:
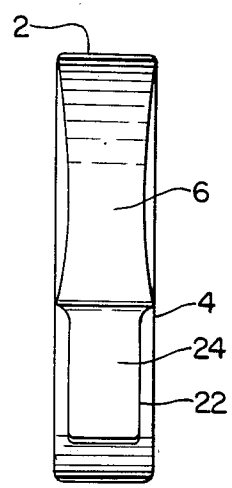
FIG. 4 is a view of the right end of the instrument, taken in the direction of arrow B of FIG. 1.

The second active blade 6 forms a unitary extension of the handle part at the opposite end of the handle from the first active blade, and extends from the handle, through an arcuate section 20 forming an angle greater than the angle formed by the handle and the first active blade, this angle being preferably approximately 150°. The outer end part of the blade is formed into a flat curve extending from the outer end of the blade for a distance of approximately 40% of the length of the blade, which is preferably approximately three inches in length, and this curved part is reduced in thickness by removal of the material of the blade and is reduced in width as shown in FIGS. 1, 2 and 4.

Use of the instrument shows it to be advantageous for improving visibility in the pterygomaxillary region, especially pterygomaxillary suture. In one procedure the pterygomaxillary suture is identified through a subperiosteal tunneling and the instrument is then placed to permit separation of the suture while the soft tissues are well retracted and protected. It is also of great utility as a retractor and protector while making bur holes osteotomies, especially in genioplasties; in intraosseous fixation techniques like the figure 8 or lateral mattresses, as in genioplasties; as a protector when reducing the palatine buttress in the downfracture of the Le Fort I osteotomy; as a protector and guide while doing the vertical subcondylar osteotomy; when using the lateral approach for the vertical subcondylar osteotomy; while making bur holes and intraosseous wire suspension form malar buttresses to maxillary arch bars, and as a protector and retractor in intraoral open reductions of mandibular fractures.

I claim:

1. A unitary instrument for the protection and retraction of the soft tissues of the oral cavity during surgery formed of thin strip stainless steel and comprising:
   (a) an elongated handle part of linear configuration,
   (b) a first active blade part connected to one end of the handle part through a curved section and forming an obtuse angle with the handle part,
   (c) a second active blade part connected to the handle part through a curved section and forming with the handle part an obtuse angle greater than the angle between the handle and the first active blade part,
   (d) each of the blade parts having at its outer end a section formed into a curve extending away from the handle part, the curved part at the outer end of the first blade part being thinner and wider than the remainder of the blade part and the curved part at the outer end of the second blade part being thinner and narrower than the remainder of the blade part.

* * * * *